United States Patent
Johnson

(10) Patent No.: US 9,186,506 B2
(45) Date of Patent: Nov. 17, 2015

(54) PORTABLE UNIT FOR TREATING CHRONIC PAIN

(75) Inventor: Robert G. Johnson, Franklinton, NC (US)

(73) Assignee: MEDFAXX, INC., Wake Forest, NC (US)

( * ) Notice: Subject to any disclaimer, the term of this patent is extended or adjusted under 35 U.S.C. 154(b) by 1963 days.

(21) Appl. No.: 12/050,463

(22) Filed: Mar. 18, 2008

(65) Prior Publication Data

US 2008/0167697 A1    Jul. 10, 2008

Related U.S. Application Data

(63) Continuation of application No. 11/196,143, filed on Aug. 3, 2005, now abandoned.

(60) Provisional application No. 60/603,138, filed on Aug. 20, 2004, provisional application No. 60/629,049, filed on Nov. 18, 2004.

(51) Int. Cl.
*A61N 1/34* (2006.01)
*A61N 1/36* (2006.01)
*A61N 1/04* (2006.01)
*A61N 1/378* (2006.01)

(52) U.S. Cl.
CPC .......... *A61N 1/36021* (2013.01); *A61N 1/0456* (2013.01); *A61N 1/378* (2013.01)

(58) Field of Classification Search
USPC ................................. 607/46, 66–70
See application file for complete search history.

(56) References Cited

U.S. PATENT DOCUMENTS

| | | | | |
|---|---|---|---|---|
| 4,249,537 A * | 2/1981 | Lee et al. | .......... | 607/64 |
| 4,580,569 A * | 4/1986 | Petrofsky | .......... | 607/48 |
| 4,595,010 A * | 6/1986 | Radke | .......... | 607/74 |
| 5,324,317 A * | 6/1994 | Reiss | .......... | 607/67 |
| 6,179,786 B1 * | 1/2001 | Young | .......... | 600/549 |
| 6,393,328 B1 * | 5/2002 | McGraw et al. | .......... | 607/72 |
| 6,445,955 B1 * | 9/2002 | Michelson et al. | .......... | 607/46 |
| 7,012,402 B2 * | 3/2006 | Miller et al. | .......... | 320/106 |
| 7,127,288 B2 * | 10/2006 | Sturman et al. | .......... | 607/2 |

OTHER PUBLICATIONS

All-Stim Device manual (2002).

* cited by examiner

*Primary Examiner* — Brian T Gedeon
(74) *Attorney, Agent, or Firm* — Myers Bigel Sibley & Sajovec, P.A.

(57) ABSTRACT

A portable pain treatment unit includes: a first pulse generator configured to deliver pulses in a frequency range typical for interferential treatment; a second pulse generator configured to deliver pulses in the frequency range for transcutaneous electrical nerve stimulator (TENS) treatment; electrodes operatively connected with the first and second pulse generators that are configured for application to a treatment area; and a power source operatively connected to the first and second pulse generators. A device of this configuration enables the patient to receive either IF or TENS treatment at a location of his/her choosing rather than being forced to receive IF treatment in a clinical setting.

8 Claims, 1 Drawing Sheet

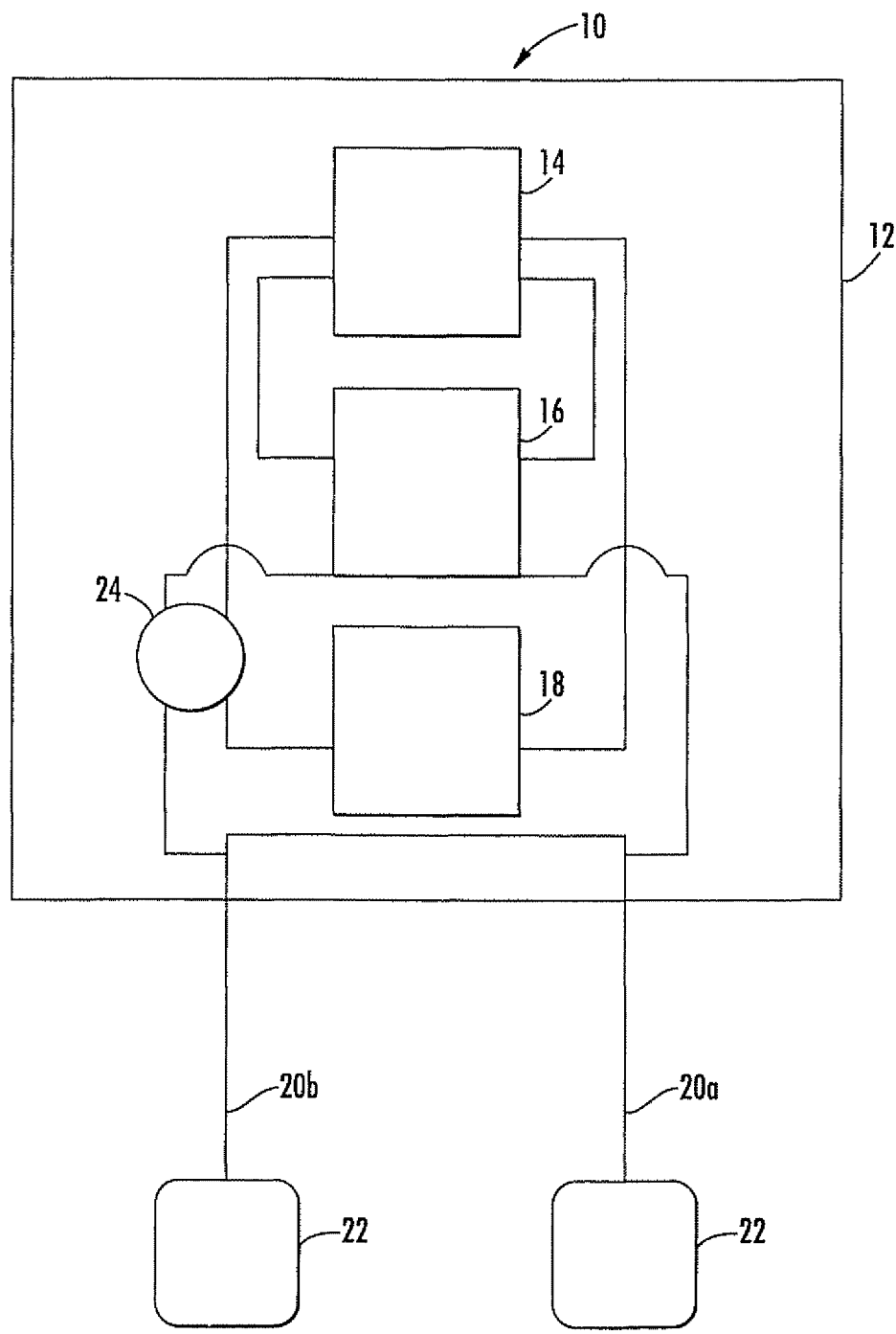

PORTABLE UNIT FOR TREATING CHRONIC PAIN

RELATED APPLICATIONS

The present application is a continuation of and claims priority from U.S. application Ser. No. 11/196,143, filed Aug. 3, 2007 entitled "Portable Unit for Treating Chronic Pain"; which claims priority from U.S. Provisional Patent Application Nos. 60/603,138, filed Aug. 20, 2004, and 60/629,049, filed Nov. 18, 2004, the disclosures of each of which are hereby incorporated herein in their entireties.

FIELD OF THE INVENTION

The present invention is directed generally to the devices for the treatment of pain, and more particularly to devices for the treatment of pain through electrical stimulation.

BACKGROUND OF THE INVENTION

The treatment of chronic pain has long been a troublesome area of medical practice. "Chronic pain" is a diagnosis that is less a true diagnosis of the physiological condition than a symptomatic diagnosis describing a chronic condition. The diagnosis often results after multiple interventions by licensed medical professionals using surgery, drugs, manipulation, stretching, chiropractic, and other modalities without substantial and/or permanent relief of the patient's pain. "Chronicity" is generally described as pain lasting for greater than 6 months, and in some cases, the time period is described as greater than 12 months.

Once a patient is diagnosed as suffering from chronic pain, often the patient is sent to a licensed professional, generally a physical therapist, who treats the patient 2 to 3 times per week in a clinic. One very common pain-treatment device is an interferential (IF) unit, which administers electrical pulses to and around the painful area. During treatment, the patient lies down and 2 to 4 electrodes are applied around the area of pain. The interferential unit then applies electrical pulses via two channels to the treatment area (typically about 5,000 to 8,500 pulses per second) for, typically, 20 to 40 minutes. The output of the two channels is configured so that the electrical currents from the two separate channels perpendicularly intersect each other in the mid-painful area, and so that the frequency of pulses differs between the channels, thereby allowing the two currents of differing orientation and frequency to interact. An exemplary interferential unit is the INTERFERENZ 5, available from Bosch.

The body is both an insulator and a conductor of electricity. At a pulse frequency of 4,000 to 5,000 pulses per second, the resistance imposed by the skin is reduced and the current can stimulate more nerves beneath the outer layer of skin. The body seems to modify the current from the two channels of an interferential unit. The resulting current from the intersection creates a new resultant waveform that alternates in amplitude and form. As a result of the current modifications the patient receives more sensory stimulation, which can relieve the pain. Generally there is a longer "carryover" period, post-treatment, in which the patient is relatively pain free, than what is achieved using other types of devices with less electrical output.

One significant shortcoming of a conventional interferential unit is its lack of portability. Viable interferential units have required alternating current for operation, as different batteries that have been tried that would enable the unit to be portable (typical 9 volt systems, including both disposable alkaline batteries and rechargeable Ni—Cd batteries) have been inadequate (some exhaust the system in less than one minute). As such, the typical setting for interferential treatment has been in a clinic, where the unit can be plugged into a wall outlet, rather than in the home or at the time of need.

One alternative unit for the treatment of chronic pain is a Transcutaneous Electrical Nerve Stimulator (TENS) device. The TENS unit is a dual channel device that typically delivers 0.5 to 200 pulses per second at a pulse width of between about 50 and 250 microseconds. The patient receives 2 to 4 electrodes around the area of pain for as long as needed. The amplitude of the TENS wave is adjusted until the patient feels sensory input that is pleasurable and not uncomfortable. If the TENS treatment benefits the patient, the physician/therapist often recommends that a TENS unit be rented and/or purchased for the patient for home use, particularly for sessions between interferential treatments.

A TENS device uses a 9 volt battery, which is sufficient because of the relative low output required for the use of this device. The TENS unit typically is a truly portable device that that the patient can wear and use on a 24 hour basis without the constraint of a lack of electrical energy due to insufficient battery capabilities. An exemplary TENS unit is the EPIX XL unit, available from EMPI, Inc.

Unfortunately, a TENS unit is generally not as effective as an interferential unit and rarely has the carryover effect achieved with the IF units. Due to this lack of "carryover relief," it is not unusual for a patient to wear a TENS unit continuously initially, then less if the underlying condition improves. Also, in many instances patients' pain relief is limited to areas between the electrodes of the TENS unit: i.e., "deep" pain (such as sciatica or other joint pain) is not relieved.

SUMMARY OF THE INVENTION

As a first aspect, the present invention is directed to a portable pain treatment unit comprising: a first pulse generator configured to deliver pulses in a frequency range typical for interferential treatment; a second pulse generator configured to deliver pulses in the frequency range for transcutaneous electrical nerve stimulator (TENS) treatment; electrodes operatively connected with the first and second pulse generators that are configured for application to a treatment area; and a power source operatively connected to the first and second pulse generators. A device of this configuration enables the patient to receive either IF or TENS treatment at a location of his/her choosing rather than being forced to receive IF treatment in a clinical setting.

As a second aspect, the present invention is directed to a TENS unit comprising: a pulse generator configured to deliver pulses in the frequency range for TENS treatment; electrodes operatively connected to the pulse generator that are configured for application to a treatment area; and a power source operatively connected to the pulse generator, wherein the pulse generator has an enhanced pulse width of at least 300 microseconds. In this configuration, the device has the capability of delivering enhanced width pulses, which can result in significant pain relief particularly for "deep" pain.

BRIEF DESCRIPTION OF THE FIGURE

The FIGURE is a schematic diagram of a pain treatment unit according to embodiments of the present invention.

DETAILED DESCRIPTION OF EMBODIMENTS OF THE INVENTION

The present invention will be described more particularly hereinafter with reference to the accompanying drawings. The invention is not intended to be limited to the illustrated embodiments; rather, these embodiments are intended to fully and completely disclose the invention to those skilled in this art. In the drawings, like numbers refer to like elements throughout. Thicknesses and dimensions of some components may be exaggerated for clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Where used, the terms "attached", "connected" "interconnected", "coupled", "contacting", "mounted" and the like can mean either direct or indirect attachment or contact between elements, unless stated otherwise.

Well-known functions or constructions may not be described in detail for brevity and/or clarity.

As used herein the expression "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring now to the FIGURE, a portable treatment unit of the present invention, designated broadly at 10, is illustrated therein. The unit 10 includes a housing 12, a power source 14, an interferential pulse generator 16, a TENS pulse generator 18, lines 20a, 20b and electrodes 22. A switch 24 enables the power source 14 to selectively energize the interferential pulse generator 16 or the TENS pulse generator 18.

The unit 10 typically employs one or two channels operating independently of each other. The waveform output of each channel may be the same waveform or a differing waveform. Generally, the waveform output will be one described as a biphasic balanced square wave or as a sinusoidal wave. All waveforms are typically balanced with a resulting net zero DC effect.

The frequency of the interferential pulse generator 16 may be adjustable in a range suitable for interferential use; typically, this range is between about 3,900 to 5,250 pulses per second per channel. The United States and most of North America, typically operates on a frequency of 4,000 to 4,250 pulses per second, but in Europe and much of Asia the frequency is between 5,000 to 5,250 pulses per second. Preferably, the unit 10 will be configured to enable the user to select frequencies for interferential pulsing within this range.

The waveforms of the pulses generated by the interferential pulse generator 16 can produce a differing, constantly changing therapeutic frequency swing pattern in the range of 0.5 to 200 pulses per second, and more specifically in the range of 50 to 180 pulses per second.

Those skilled in this art will understand the basic structure and operation of the interferential pulse generator 16, which need not be described in any further detail herein.

The TENS pulse generator 18 will typically use the same or similar waveforms as the interferential pulse generator 16. The frequency is typically between 0.5 to 300 pulses per second and the width of each pulse is in the range of 50 to 350 microseconds. Optionally, there may be frequency modulator in the unit 10 to induce modulation that occurs in the rate and/or width of each frequency and pulse width.

In some embodiments, it may be desirable for the TENS pulse generator 18 to generate pulses having a width greater than 250 microseconds; a pulse width in the range of 250 or 300 to 800 or 1,000 microseconds may be preferred. While not wishing to be bound by any theory of operation, it is theorized that increased pulse width can allow stimulation to the underlying nerves with a sufficient strength to create sensory input in the region. The output of TENS units is typically measured against an impedance of 500 ohms of resistance in almost all literature provided by manufacturers/suppliers. However, the skin itself can produce an impedance of 5 to 10 times that amount, and as a result of that impedance the actual wave form of a conventional TENS unit may be, and often is, seriously degraded. Typically, the wave form produced by a conventional TENS unit is modeled as a square wave, but in practice in the target area under the skin of the patient the wave form more resembles a spike than a square. This serious degradation of the wave can result in limited success, and in many instances no success, due to the fact a conventional TENS unit is not sufficiently strong to overcome the typical skin impedance. However, by increasing the pulse width of the TENS wave above 250 microseconds as described above, the skin's resistance can be overcome and depolarization can occur in the target areas. When this occurs the patient often verbalizes to the clinician that the sensation is "going deeper and farther". This sensory perception means the patient can now feel the sensation in the same area that the pain is felt. This can be beneficial to achieving pain relief for a patient.

More specifically, the potential benefits that may be derived from a wider pulse width include: greater sensory input in the entire affected pain area; increased cell/nerve permeability for ionic and molecular transfer; increased fluid absorption/disbursement in edematous patients; enhanced chemical interactions in specific area; greater sensory desensitization of nerve fibers; and increased opioid peptide release of pain regulators with higher width and lower pulse rate.

Referring again to the FIGURE, the power source 14 comprises a battery or similar power cell. In some embodiments, the power source 14 will comprise a rechargeable battery system capable of powering the interferential pulse generator 16 of the unit 10. It is preferred that the unit 10 be portable, so the power source 14 should be selected to accommodate portability. Exemplary batteries are AA and AAA batteries, in particular rechargeable NiMh (nickel metal hydride) batteries; these can be obtained, for example, from GP Battery (Model GP 2100) or Sanyo. It should also be understood that the power source 14 may be configured to use AC current (for example, from a wall outlet) if the user desires.

The electrodes 22 are connected to the pulse generators 16, 18 via the lines 20a, 20b. The electrodes 22 can be any electrodes known by those skilled in this art to be suitable for applying therapeutic electrical pulses to a patient.

The switch 24 can enable the user to choose between an interferential treatment or a TENS treatment for most efficacious treatment. The switch 24 can be any conventional switch known to those skilled in this art to be suitable for such use and need not be described in greater detail herein.

Also, the configuration of the unit 10 shown herein is illustrative only; other interconnections between the power source 14, the interferential unit 16, the TENS unit 18, the electrodes 22, and the switch 24 recognized by those skilled in this art to enable the user to convert between TENS unit 18 and the interferential unit 16 may also be employed. For example, separate power sources may be included for TENS and interferential unit operation.

The unit 10 can enable the user to select a treatment mode (i.e., interferential or TENS) as desired, without having to visit a clinic for interferential treatment.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention.

That which is claimed is:

1. A portable pain treatment unit, comprising:
   a first pulse generator configured to deliver pulses in a frequency range typical for interferential treatment;
   a second pulse generator configured to deliver pulses in the frequency range for transcutaneous electrical nerve stimulator (TENS) treatment;
   electrodes operatively connected with the first and second pulse generators that are configured for application to a treatment area; and
   a power source operatively connected to the first and second pulse generators;
   wherein the unit is configured such that the first pulse generator and the second pulse generator deliver pulses separately and independently of each other.

2. The treatment unit defined in claim 1, wherein the second pulse generator is configured to provide a pulse width of at least 300 microseconds.

3. The treatment unit defined in claim 1, wherein the power source comprises a nickel metal hydride battery.

4. The treatment unit defined in claim 3, wherein the battery is a 9-volt battery.

5. The treatment unit defined in claim 1, wherein the unit comprises two electrodes.

6. The treatment unit defined in claim 1, wherein the first pulse generator is configured to deliver pulses in the frequency range between about 3,900 and 5,250 Hz per channel.

7. The treatment unit defined in claim 1, wherein the second pulse generator is configured to deliver pulses in the frequency range between about 0.5 and 300 Hz.

8. The treatment unit defined in claim 1, further comprising a switch configured to alternatively activate the first pulse generator or the second pulse generator.

\* \* \* \* \*